(12) United States Patent
Wakai et al.

(10) Patent No.: US 10,660,660 B2
(45) Date of Patent: May 26, 2020

(54) DETECTOR-EQUIPPED TREATMENT TOOL

(71) Applicant: OLYMPUS CORPORATION, Tokyo (JP)

(72) Inventors: Hiroshi Wakai, Tokyo (JP); Masatoshi Iida, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 299 days.

(21) Appl. No.: 15/619,736

(22) Filed: Jun. 12, 2017

(65) Prior Publication Data

US 2017/0273700 A1    Sep. 28, 2017

Related U.S. Application Data

(63) Continuation of application No. PCT/JP2014/084704, filed on Dec. 26, 2014.

(51) Int. Cl.
*A61B 17/28*    (2006.01)
*A61B 34/00*    (2016.01)
(Continued)

(52) U.S. Cl.
CPC ............ *A61B 17/28* (2013.01); *A61B 1/0055* (2013.01); *A61B 34/37* (2016.02); *A61B 34/76* (2016.02); *A61M 25/09033* (2013.01); *A61B 1/018* (2013.01); *A61B 10/04* (2013.01); *A61B 2017/003* (2013.01);
(Continued)

(58) Field of Classification Search
CPC ......... A61B 17/28; A61B 17/29; A61B 34/76; A61B 34/37; A61B 2090/065; A61B 2017/2932; A61B 2017/2939; A61B 2017/2947; A61B 2017/2926; A61B 2017/00022
See application file for complete search history.

(56) References Cited

U.S. PATENT DOCUMENTS 6,669,690 B1    12/2003    Okada et al.
2004/0138594 A1   7/2004    Sekino et al.
(Continued)

FOREIGN PATENT DOCUMENTS

EP    1 426 014 A2    6/2004
JP    H08-224244 A    9/1996
(Continued)

OTHER PUBLICATIONS

Japanese Office Action dated Jul. 24, 2018 in Japanese Patent Application No. 2016-565854.
International Search Report dated Feb. 3, 2015 issued in PCT/JP2014/084704.

*Primary Examiner* — Katherine M Rodjom
(74) *Attorney, Agent, or Firm* — Scully, Scott, Murphy & Presser, P.C.

(57) ABSTRACT

A detector-equipped treatment tool including: a distal-end treatment portion that applies a force to and treats biological tissue; a proximal-end portion that supports the distal-end treatment portion so as to be relatively movable; a detector that is disposed in a cavity provided inside of the distal-end treatment portion and detects the force; wiring that is connected to the detector; and a duct that is connected to the distal-end treatment portion and guides the wiring led out of the distal-end treatment portion from the detector in the cavity to the proximal-end portion.

6 Claims, 7 Drawing Sheets

(51) Int. Cl.
*A61B 34/37* (2016.01)
*A61B 1/005* (2006.01)
*A61M 25/09* (2006.01)
*A61B 1/018* (2006.01)
*A61B 90/00* (2016.01)
*A61B 17/29* (2006.01)
*A61B 34/30* (2016.01)
*A61B 10/04* (2006.01)
*A61B 17/00* (2006.01)

(52) U.S. Cl.
CPC .............. *A61B 2017/00022* (2013.01); *A61B 2017/2926* (2013.01); *A61B 2017/2939* (2013.01); *A61B 2017/2943* (2013.01); *A61B 2034/301* (2016.02); *A61B 2090/065* (2016.02)

(56) References Cited

U.S. PATENT DOCUMENTS

| | | |
|---|---|---|
| 2005/0004589 A1 | 1/2005 | Okada et al. |
| 2005/0021078 A1* | 1/2005 | Vleugels ............... A61B 17/29 606/205 |
| 2007/0016235 A1 | 1/2007 | Tanaka et al. |
| 2010/0324458 A1 | 12/2010 | Okada et al. |
| 2011/0004127 A1 | 1/2011 | Okada et al. |
| 2012/0172873 A1* | 7/2012 | Artale ............... A61B 18/1442 606/46 |
| 2015/0209573 A1* | 7/2015 | Hibner ................... A61N 1/00 606/48 |

FOREIGN PATENT DOCUMENTS

| | | |
|---|---|---|
| JP | H09-098979 A | 4/1997 |
| JP | 2004-180997 A | 7/2004 |
| JP | 3756556 B2 | 3/2006 |
| JP | 2006-158525 A | 6/2006 |

* cited by examiner

DETECTOR-EQUIPPED TREATMENT TOOL

CROSS-REFERENCE TO RELATED APPLICATIONS

This is a continuation of International Application PCT/JP2014/084704 which is hereby incorporated by reference herein in its entirety.

TECHNICAL FIELD

The present invention relates to a detector-equipped treatment tool.

BACKGROUND ART

There are known detector-equipped gripping forceps that are provided with a cavity in the back side of a gripping surface and that detect a gripping force by using a strain sensor embedded in the cavity (for example, refer to PTL 1).

In the gripping forceps of PTL 1, wiring connected to the strain sensor is led out of the cavity portion at the back side of the gripping surface, and the wiring led out of the cavity portion is guided to the proximal-end side of a treatment tool in the form of free-space wiring.

CITATION LIST

Patent Literature

{PTL 1} Publication of Japanese Patent No. 3756556

SUMMARY OF INVENTION

An aspect of the present invention is a detector-equipped treatment tool including: a distal-end treatment portion that applies a force to and treats biological tissue; a proximal-end portion that supports the distal-end treatment portion so as to be relatively movable; a detector that is disposed in a cavity provided inside of the distal-end treatment portion and that detects the force; wiring that is connected to the detector; and a duct that is connected to the distal-end treatment portion and that guides the wiring led out of the distal-end treatment portion from the detector in the cavity to the proximal-end portion.

DESCRIPTION OF EMBODIMENTS

A detector-equipped treatment tool 3 according to an embodiment of the present invention will be described below with reference to the drawings.

Figure 1:
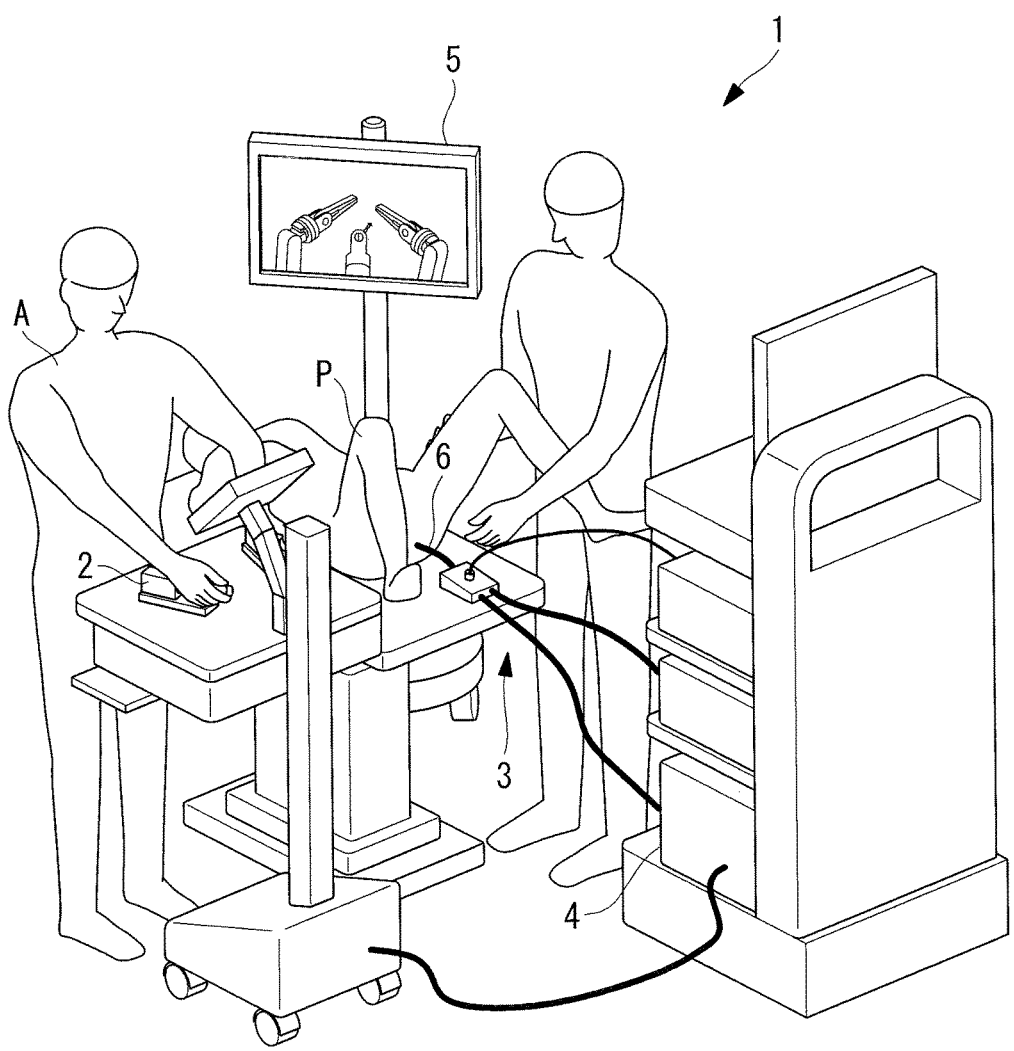
FIG. 1 is an overall configuration diagram showing a medical manipulator system including a detector-equipped treatment tool according to an embodiment of the present invention.

The detector-equipped treatment tool 3 according to this embodiment is gripping forceps and is used, for example, in a medical manipulator system 1 shown in FIG. 1. This medical manipulator system 1 includes a master device 2 that is operated by an operator A, the detector-equipped treatment tool 3 that is inserted in the body cavity of a patient P, a control portion 4 that controls the detector-equipped treatment tool 3 on the basis of an operation input to the master device 2, and a monitor 5.

Figure 2A:
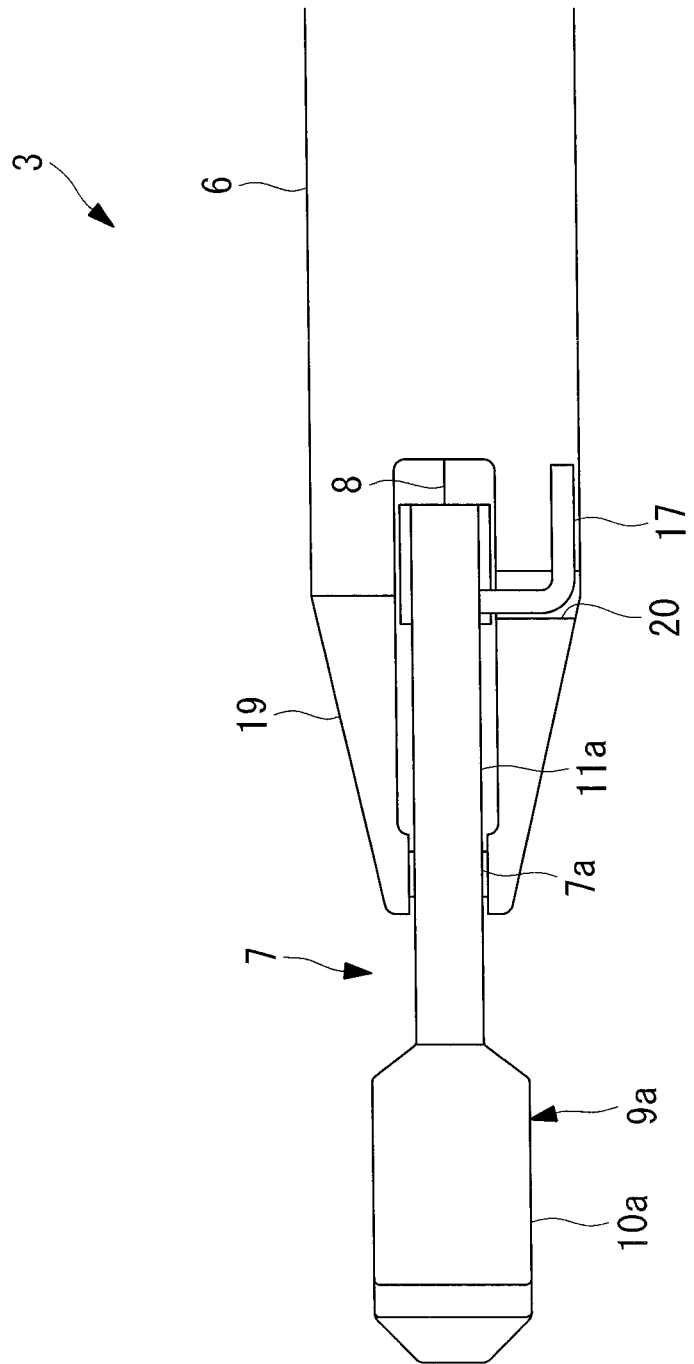
FIG. 2A is a front view showing the distal-end treatment portion of the detector-equipped treatment tool in FIG. 1.
Figure 2B:
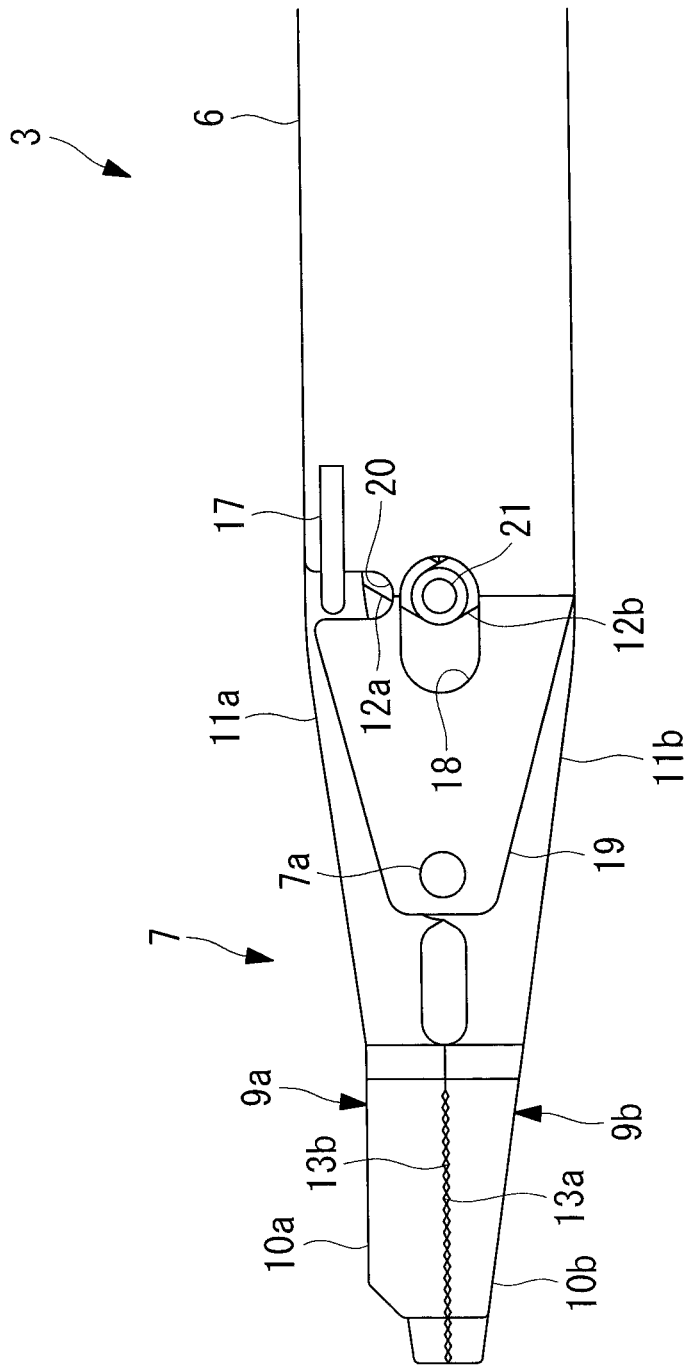
FIG. 2B is a side view showing the distal-end treatment portion of the detector-equipped treatment tool in FIG. 2A.

As shown in FIGS. 2A and 2B, the detector-equipped treatment tool 3 according to this embodiment includes, for example: an elongated insertion portion (proximal-end portion) 6 that is inserted in the body cavity of the patient P via a forceps channel of an endoscope inserted in the body cavity of the patient P; a distal-end treatment portion 7 that is disposed at the distal end of the insertion portion 6; a driving portion (not shown) that is disposed at the proximal end of the insertion portion 6 and that operates the distal-end treatment portion 7 by being controlled by the control portion 4; and a driving-force transmitting member 8 such as a wire that transmits a driving force generated by the driving portion to the distal-end treatment portion 7.

Figure 3A:
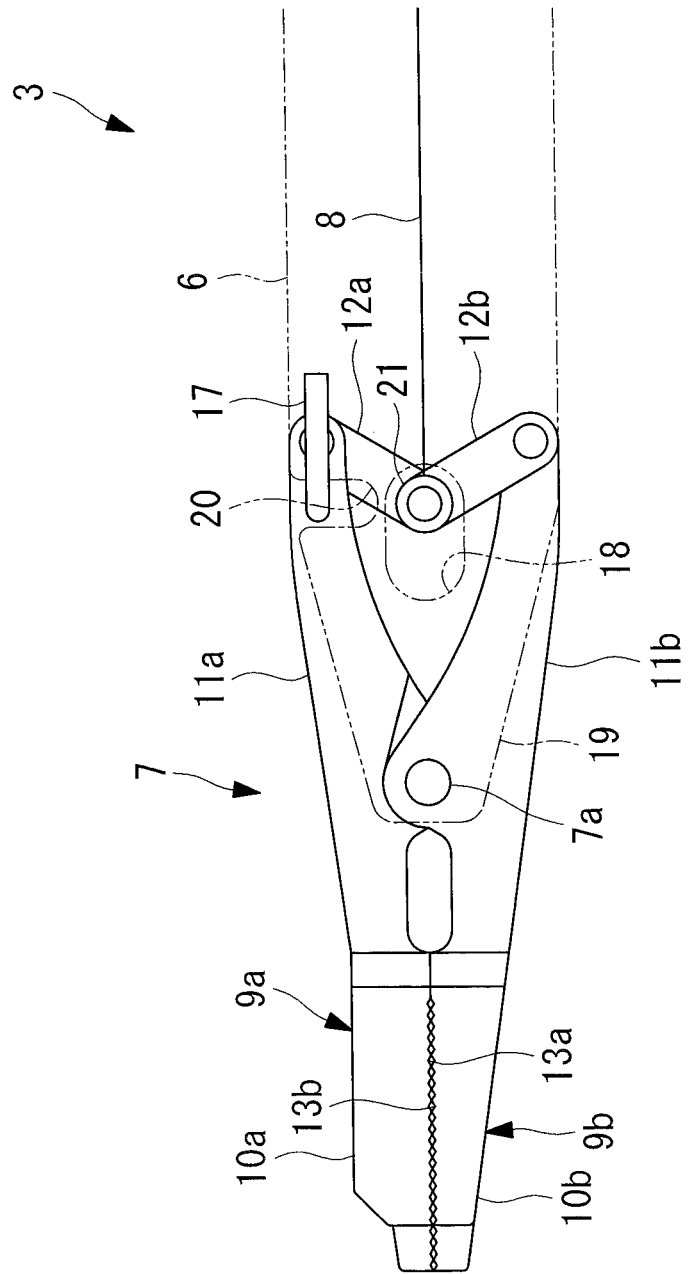
FIG. 3A is a side view for explaining a link mechanism of the distal-end treatment portion of the detector-equipped treatment tool in FIG. 2B.
Figure 3B:
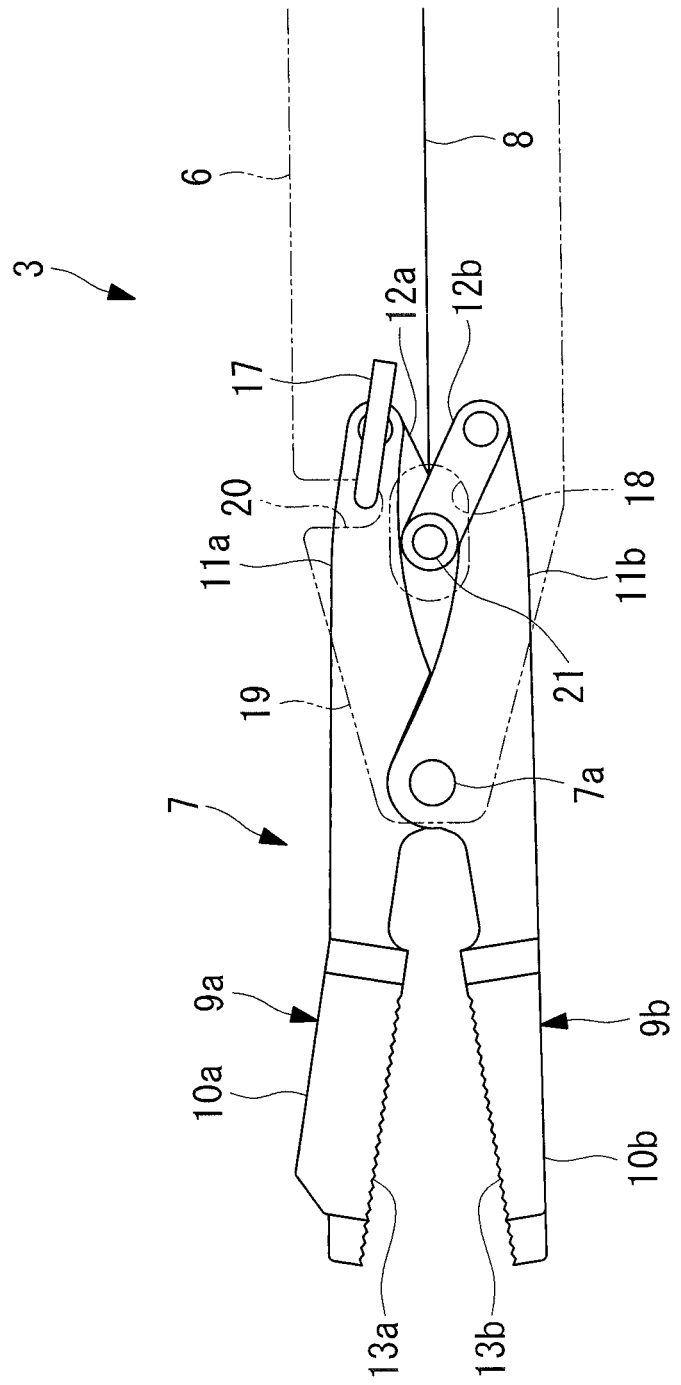
FIG. 3B is a side view showing a state in which the distal-end treatment portion is open due to the operation of the link mechanism in FIG. 3A.
Figure 4A:
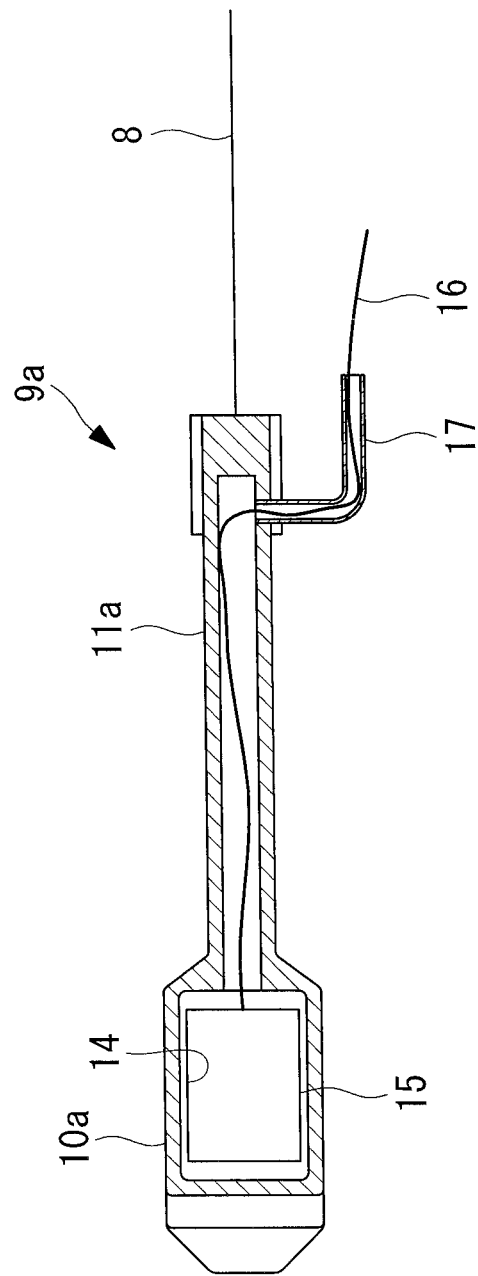
FIG. 4A is a partially cut-away sectional view for explaining a strain gauge and a wiring path in the distal-end treatment portion of the detector-equipped treatment tool in FIG. 1.
Figure 4B:
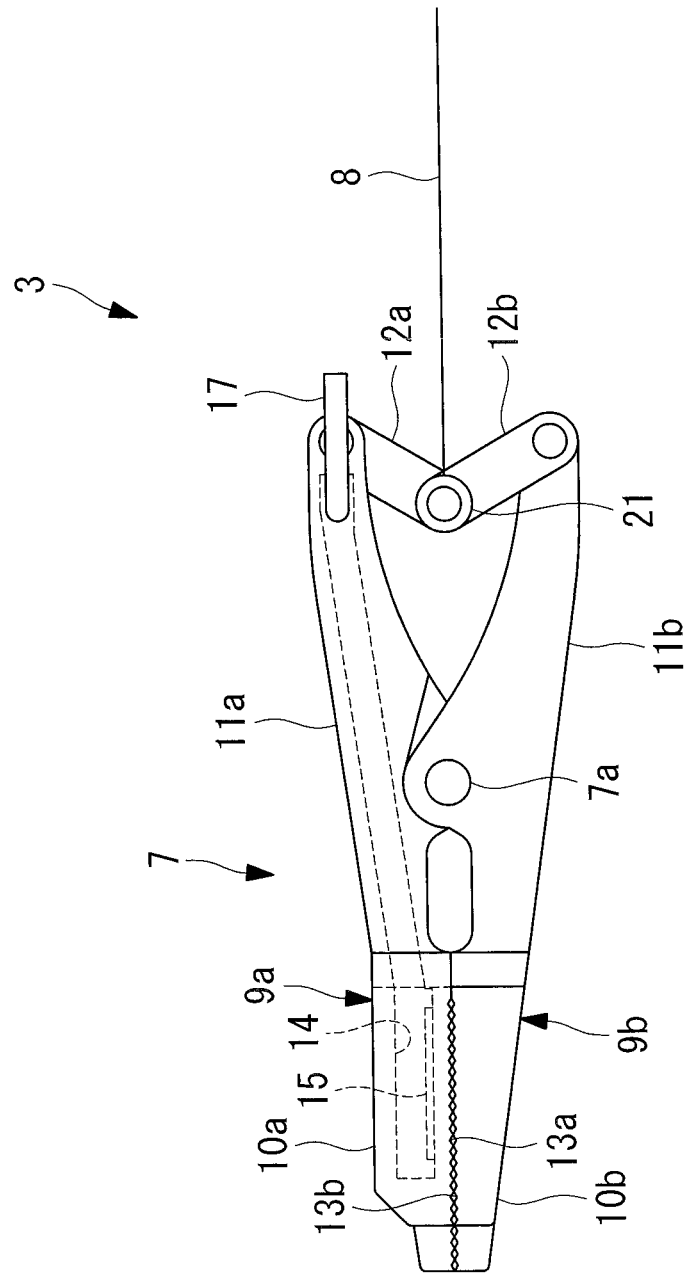
FIG. 4B is a side view of the distal-end treatment portion for explaining the strain gauge and the wiring path in FIG. 4A.

As shown in FIGS. 2A-4B, the distal-end treatment portion 7 includes two gripping pieces 9a, 9b attached to the distal end of the insertion portion 6 so as to be swivelable about a swivel shaft 7a disposed orthogonally to the longitudinal axis of the insertion portion 6. As shown in FIGS. 3 and 4, the gripping pieces 9a, 9b respectively include gripping portions 10a, 10b that grip biological tissue therebetween and that are disposed closer to the distal-end side than the swivel shaft 7a is and extension portions 11a, 11b that extend further toward the proximal-end side than the swivel shaft 7a. The other ends of two links 12a, 12b, one ends of which are connected via a movable shaft 21 so as to be relatively swivelable, are respectively connected to the proximal-ends of the extension portions 11a, 11b so as to be swivelable, and the driving-force transmitting member 8 is connected to the movable shaft 21.

That is, a booster device (drive mechanism) is formed for driving the distal-end treatment portion 7 with respect to the insertion portion 6 by using a quadric link in which the two extension portions 11a, 11b of the distal-end treatment portion 7 and the two links 12a, 12b are mutually connected. As shown in FIG. 3B, in a state in which gripping surfaces 13a, 13b of the two gripping portions 10a, 10b are spaced from each other, by applying a tension force to the movable shaft 21 through a wire 8, the two links 12a, 12b are caused to swivel in such a way that the relative angle therebetween is expanded, as shown in FIG. 3A. As a result, proximal ends of the two extension portions 11a, 11b are pushed in a direction in which the proximal ends are spaced from each other, thereby biasing the two gripping portions 10a, 10b of the distal-end treatment portion 7 in directions in which the gripping surfaces 13a, 13b are pressed against each other.

In addition, in this embodiment, as shown in FIGS. 4A and 4B, a cavity portion 14 is provided inside of at least the gripping portion 10a of the gripping portions, and a detector such as a strain gauge 15 is affixed to the inside of the cavity portion 14 arranged on the back side of the gripping surface 13a. As the strain gauge 15, for example, one that outputs a detected strain amount as a digital signal is preferable.

In addition, in this embodiment, the cavity portion 14 extends inside the gripping piece 9a along the length direction, and wiring 16 connected to the strain gauge 15 is guided through the cavity portion 14 to the proximal-end side of the extension portion 11a of the gripping piece 9a.

By outputting a digital signal from the strain gauge 15, it is possible to decrease the number of wires so as to make the cavity portion 14 narrower, and it is also possible to detect the gripping force with high precision while maintaining the rigidity of the gripping piece 9a.

In addition, a duct 17 extending from the side surface of the gripping piece 9a in a direction parallel to the swivel shaft 7a is provided near the portion connecting to the link 12a at the proximal-end side of the extension portion 11a so as to be connected to the cavity portion 14, and the wiring 16 in the cavity portion 14 is routed through the duct 17 to the outside of the gripping piece 9a. The duct 17 is curved toward the proximal-end side so that the wiring 16 led out of the duct 17 can be routed easily in a direction along the insertion portion 6.

As shown in FIGS. 2A-3B, a bracket 19 for attaching the two gripping pieces 9a, 9b to the distal end of the insertion portion 6 so as to be swivelable is provided with a notch 20 so as to avoid interference with the duct 17, which moves due to the swivel of the gripping piece 9a. In the figures, reference sign 18 denotes a long hole provided in the bracket 19 over the moving range of the movable shaft 21 so as to avoid interference between the movable shaft 21 and the bracket 19 at the connecting portion between the links 12a and 12b.

The operation of the thus-configured detector-equipped treatment tool 3 according to this embodiment will be described.

In order to perform treatment of an affected site in the body of the patient P by using the detector-equipped treatment tool 3 according to this embodiment, an insertion portion of an endoscope, which is not shown, is inserted into the body cavity of the patient P, and the detector-equipped treatment tool 3 is inserted into the body of the patient P via a forceps channel in the insertion portion.

Then, in a state in which the distal-end treatment portion 7 of the detector-equipped treatment tool 3 is disposed close to the affected site in the body cavity, the operator A operates the master device 2 while checking images acquired by using the endoscope on the monitor 5, so as to cause the driving portion to operate, change a tension force applied to the wire 8, and cause the two gripping pieces 9a, 9b to swivel around the swivel shaft 7a, thereby opening and closing the gripping portions 10a, 10b and treating the affected site.

In this case, when the master device 2 is operated so as to increase the tension force generated in the wire 8, and biological tissue is gripped with the gripping portions 10a, 10b, deformation of the gripping surface 13a is detected by the strain gauge 15 disposed on the back side of at least the gripping portion 13a of the gripping portions. This makes it possible to estimate the force being applied to the biological tissue gripped between the gripping surfaces 13a, 13b.

In particular, in a case where the insertion portion 6 is a flexible portion, friction between the wire 8 passing through the insertion portion 6, which is curved along the shape of the curved body cavity, and a path in the insertion portion 6 changes depending on the curved shape, and thus, it is not necessarily possible to grip the biological tissue with the same force even when the same force is applied at the master device 2.

In this case, by estimating, with the detector 15, the force being applied to the biological tissue, it becomes possible to feed back the information relating to the estimated force to the control portion 4 so that the tension force generated in the wire 8 can be adjusted, and as a result, it becomes possible to apply, to the biological tissue, a gripping force corresponding to the force applied at the master device 2 regardless of the curvature state of the insertion portion 6.

In addition, the detector-equipped treatment tool 3 according to this embodiment has an advantage in that it is possible not to expose the wiring 16 near the gripping portions 10a, 10b of the distal-end treatment portion 7 contacting the biological tissue during the treatment because the wiring 16 connected to the strain gauge 15 is guided through the cavity portion 14 inside the gripping piece 9a to the proximal-end side of the extension portion 11a and is led out to the outside of the gripping piece 9a through the duct 17. As a result, the wiring 16 does not contact the biological tissue during the treatment, and a physical or chemical load applied to the wiring 16 is reduced, and thus, it is possible to prevent damage to the wiring 16.

Because a portion led out from the extension portion 11a, which is a movable portion, is led out via the duct 17 secured to the extension portion 11a, the wiring 16 is less likely to interfere with surrounding biological tissue or the like due to the movement of the extension portion 11a. In addition, because the duct 17 is extended from the side surface of the gripping piece 9a so as to be parallel to the swivel shaft 7a, the duct 17 is not positioned where the duct 17 is sandwiched between the gripping piece 9a and the biological tissue even when the gripping piece 9a is caused to swivel, and thus, the duct 17 is protected by the gripping piece 9a.

The duct 17 is protected by the bracket 19 because the duct 17 moves within the notch 20 in the bracket 19. Therefore, there is an advantage in that it is possible to prevent damage to the wiring 16 due to contact with the biological tissue and to facilitate treatment by reliably detecting the force applied to the biological tissue.

Note that, although gripping forceps causing two gripping pieces 9a, 9b to swivel have been illustrated in this embodiment, alternatively, this embodiment may be applied to gripping forceps causing a single gripping piece to swivel, or to any other detector-equipped treatment tool. In addition, a detector-equipped treatment tool provided with the strain gauge 15 on both of the two gripping pieces 9a, 9b may be employed.

In addition, the outlet from which the wiring 16 is led out of the duct 17 or the inside of the cavity portion 14 may be sealed with resin or the like. In addition, the gripping force estimated on the basis of the strain detected by the strain gauge 15 may be transmitted to the operator A through feedback to the master device 2 (force feedback). In addition, the magnitude of the force may be reported to the operator A through image display, waveform display, voice, light or the like.

In addition, because the duct 17 is provided at the extension portion 11a, and the extension portion 11a constitutes part of a quadric link, it is possible to simplify the structure by sharing a booster device and a path member for the wiring 16, thereby reducing the size of the distal-end portion. Alternatively, the booster device and the path member for the wiring 16 may be provided separately.

The above-described embodiment leads to the following invention.

An aspect of the present invention is a detector-equipped treatment tool including: a distal-end treatment portion that applies a force to and treats biological tissue; a proximal-end portion that supports the distal-end treatment portion so as to be relatively movable; a detector that is disposed in a cavity provided inside of the distal-end treatment portion and that detects the force; wiring that is connected to the detector; and a duct that is connected to the distal-end treatment portion and that guides the wiring led out of the distal-end treatment portion from the detector in the cavity to the proximal-end portion.

With this aspect, when the distal-end treatment portion is made to contact the biological tissue, and the force is applied to the biological tissue by moving the distal-end treatment portion relative to the proximal-end portion, the force is detected by the detector disposed in the cavity portion provided inside of the distal-end treatment portion, and the detected force information is led out from the inside of the cavity portion to the outside of the distal-end treatment portion through the wiring connected to the detector and is guided to the proximal-end side through the duct. The force information taken out through the wiring is used for purposes such as adjusting the force applied to the biological tissue from the distal-end treatment portion through feedback.

In this case, in this embodiment, because the wiring led out from the inside of the cavity portion of the distal-end treatment portion is not exposed to the outside as free-space wiring but is guided through the duct, it is possible to avoid direct contact between the wiring and the biological tissue. Therefore, it is possible to prevent damage to the wiring due to contact with the biological tissue and to facilitate treatment by reliably detecting the force applied to the biological tissue from the distal-end treatment portion.

In the above-described aspect, the distal-end treatment portion may include an extension portion that is provided at the proximal-end portion so as to be swivelable around a predetermined axis and that extends further toward a proximal-end side than the axis, and the duct may be connected to the extension portion.

By doing so, the wiring connected to the detector is guided through the inside of the cavity portion in the distal-end treatment portion to the extension portion, and is led out from the distal-end treatment portion via the duct connected to the extension portion. The site that contacts the biological tissue when treatment is performed using the distal-end treatment portion is positioned closer to the distal-end side than the axis around which the distal-end treatment portion is caused to swivel is, and thus, the number of times that the extension portion positioned closer to the proximal-end side than the axis is contacts the biological tissue is reduced. Therefore, due to the duct being connected to the extension portion, the number of times that the duct contacts the biological tissue is reduced, and thus, the number of times that a physical force is applied to the duct is reduced. As a result, it becomes possible to more reliably protect the wiring.

In addition, the above-described aspect may further include a drive mechanism that drives the distal-end treatment portion with respect to the proximal-end portion, wherein the extension portion may constitute part of the drive mechanism.

By doing so, when the drive mechanism is caused to operate, the force acting on the extension portion constituting part of the drive mechanism causes the distal-end treatment portion to swivel around the axis, with the extension portion serving as a lever, and the biological tissue is treated by being pressed by the distal-end treatment portion. By further using the extension portion constituting part of the drive mechanism as a path for leading out the wiring, it becomes possible to simplify the structure and reduce the size of the distal-end treatment portion.

In addition, in the above-described aspect, the duct may be connected to a side surface of the extension portion in the direction of the axis.

By doing so, when the distal-end treatment portion is caused to swivel with respect to the proximal-end portion, the extension portion serving as part of the distal-end treatment portion is also caused to swivel. As a result, the distal-end treatment portion becomes closer to the biological tissue arranged in the swivel direction when the distal-end treatment portion is caused to swivel in one direction. However, by connecting the duct to the side surface, the duct is prevented from being pressed against the biological tissue, and thus, damage can be prevented more reliably.

In addition, in the above-described aspect, the distal-end treatment portion may be two gripping portions that are supported so as to be swivelable relative to the proximal-end portion and that grip the biological tissue therebetween.

By doing so, the gripping force when the biological tissue is gripped between the two gripping portions can be detected by the detector. Because the wiring is less likely to be damaged, it is possible to facilitate treatment by reliably detecting the gripping force applied to the biological tissue.

REFERENCE SIGNS LIST 3 detector-equipped treatment tool
6 insertion portion (proximal-end portion)
7 distal-end treatment portion
7a swivel shaft (axis)
10a, 10b gripping portions
11a, 11b extension portions
14 cavity portion (cavity)
15 strain gauge (detector)
16 wiring
17 duct

The invention claimed is:
1. A detector-equipped treatment tool comprising:
a grasper having a first jaw and a second jaw, wherein at least one of the first jaw and the second jaw is movable relative to the other of the first jaw and the second jaw to apply a force to biological tissue and to treat the biological tissue;
an insertion portion that supports the grasper;
a sensor disposed in a cavity enclosed within the grasper for detecting the force;
wiring connected to the sensor; and
a duct connected to the grasper;
wherein the cavity extends inside the grasper and is in communication with the duct;
the wiring is routed from the cavity and through the duct to an outside of the grasper;
the wiring routed to the outside of the grasper is routed inside the insertion portion such that the wiring is connected to a controller configured to control the force applied to the biological tissue by the grasper;
the grasper includes at least one extension, the at least one extension being swivelable around a predetermined axis, the at least one extension extending further toward a proximal-end side than the predetermined axis;
the duct extends from the at least one extension; and the duct has a first portion extending from a side surface of the at least one extension in the direction of the predetermined axis.

2. The detector-equipped treatment tool according to Claim 1, further comprising:
a drive linkage that drives the grasper to apply the force to the biological tissue,
wherein the at least one extension constitutes part of the drive-linkage.

3. The detector-equipped treatment tool according to Claim 1, wherein the cavity is provided in the first jaw.

4. The detector-equipped treatment tool according to claim 3, wherein the at least one extension is provided to extend from the first jaw and the cavity extends from the first jaw and through the at least one extension.

5. The detector-equipped treatment tool according to Claim 1, wherein the duct has a second portion extending from the first portion, the second portion extending in a direction along a longitudinal axis of the insertion portion.

6. The detector-equipped treatment tool according to claim 1, wherein the sensor is a strain gauge.

* * * * *